United States Patent
Witte

(10) Patent No.: US 9,345,856 B2
(45) Date of Patent: May 24, 2016

(54) MEDICAL CATHETER WITH REDUCED BACKFLOW

(75) Inventor: Jens Witte, Munich (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 14/115,887

(22) PCT Filed: May 16, 2011

(86) PCT No.: PCT/EP2011/057814
§ 371 (c)(1),
(2), (4) Date: Nov. 6, 2013

(87) PCT Pub. No.: WO2012/155954
PCT Pub. Date: Nov. 22, 2012

(65) Prior Publication Data
US 2014/0107610 A1 Apr. 17, 2014

(51) Int. Cl.
A61M 31/00 (2006.01)
A61M 5/14 (2006.01)
A61M 25/00 (2006.01)
A61M 25/04 (2006.01)
A61B 17/00 (2006.01)

(52) U.S. Cl.
CPC ........... *A61M 25/0043* (2013.01); *A61M 25/04* (2013.01); *A61B 2017/00986* (2013.01); *A61M 25/007* (2013.01); *A61M 2025/0004* (2013.01)

(58) Field of Classification Search
CPC .............. A61M 25/04; A61M 25/007; A61M 2025/0004; A61M 2025/0024; A61M 2025/0063; A61M 25/0043; A61M 25/0054; A61B 2017/3484; A61B 2017/00986; A61J 15/0015; A61J 15/0038
USPC ........................................................ 604/500
See application file for complete search history.

(56) References Cited

U.S. PATENT DOCUMENTS

| | | | |
|---|---|---|---|
| 2003/0093104 A1 * | 5/2003 | Bonner | A61B 17/3478 606/185 |
| 2005/0085771 A1 * | 4/2005 | Lyon | A61B 17/3421 604/107 |
| 2009/0088730 A1 | 4/2009 | Hoofnagle et al. | |

FOREIGN PATENT DOCUMENTS

| | | | | |
|---|---|---|---|---|
| GB | 2 428 198 | | 1/2007 | |
| GB | 2428198 A | * | 1/2007 | ......... A61B 17/3415 |
| WO | 2007/081468 | | 7/2007 | |

OTHER PUBLICATIONS

International Search Report for International Application No. PCT/EP2011/057814 dated Feb. 1, 2012.

* cited by examiner

*Primary Examiner* — Jason Flick
(74) *Attorney, Agent, or Firm* — Tucker Ellis LLP

(57) ABSTRACT

A medical catheter (1) comprising an inner catheter tube (2) and an outer catheter tube (3), wherein the inner catheter tube (2) has at least one outlet port (6) for a medical liquid at its distal end and the outer catheter tube comprises two parts of differing rigidities, namely a flexible part (5) and a rigid part (4), wherein the flexible (5) part is located at the distal end of the outer catheter tube (3) and the distal end of the flexible part (5) is connected to the inner catheter tube (2), and wherein the medical catheter also comprises a drive means (7) for generating a relative movement between the inner catheter tube (2) and the rigid part (4) of the outer catheter tube (3).

13 Claims, 3 Drawing Sheets

MEDICAL CATHETER WITH REDUCED BACKFLOW

Figure 1:
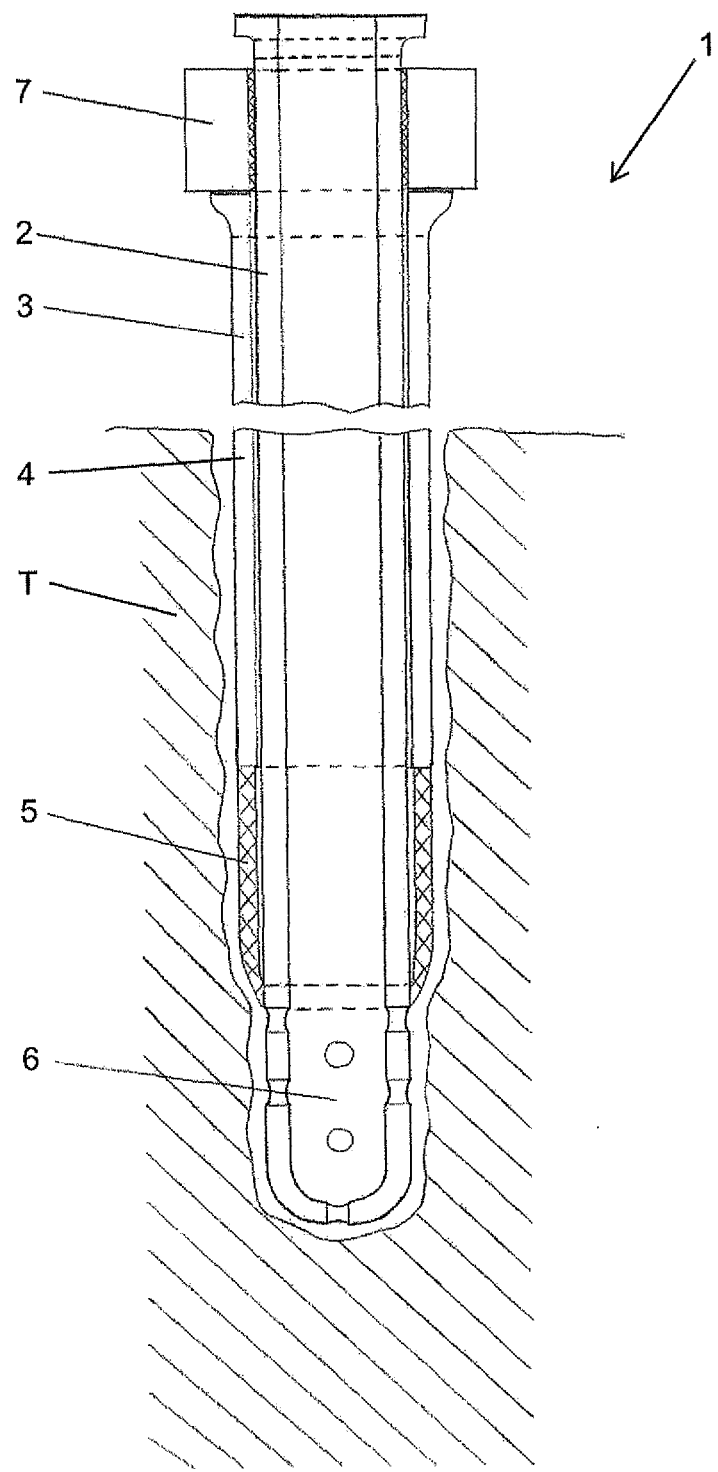

This application is a national phase of International application No. PCT/EP2011/057814 filed May. 16, 2011 and published English language.

The present invention relates to a medical catheter in which backflow is reduced or even prevented and to a method for reducing backflow when using a catheter.

Catheters have been used for decades to administer medical liquids into tissue. For this purpose, the catheter is partly inserted into the tissue, for example using a stylet to reinforce the catheter during insertion. When the tip of the catheter is forced into the tissue, a gap is created between the tissue and the catheter. When the medical liquid is then delivered through an outlet port at the tip of the catheter, a part of the medical liquid flows back through the gap along the catheter instead of propagating into the tissue close to the outlet port. This effect is called backflow and is highly undesirable because it creates a discrepancy between the course of the actual injection and the treatment plan.

It is therefore an object of the present invention to provide a medical catheter and a method which reduce, and preferably completely prevent, backflow.

This problem is solved by the medical catheter and method according to the independent claims. Advantageous embodiments are defined in the dependent claims.

The medical catheter according to the present invention comprises an inner catheter tube and an outer catheter tube. The inner and outer catheter tubes are preferably concentric, wherein the word "concentric" is understood to mean that, in a cross-section perpendicular to the axial (or longitudinal) extension of the catheter, the inner catheter tube lies completely within the outer catheter tube. The longitudinal axes of the two catheter tubes need not be but are preferably identical. Alternatively, the inner and outer catheter tubes can also be arranged next to each other. In general, there can be a gap between the inner and outer catheter tubes, at least along a part of their axial extension, or the two tubes can be in abutment.

The catheter has two ends: a distal end, i.e. the tip which is to be inserted into the tissue; and a proximal end, which is accordingly the opposite end of the catheter to its tip.

The inner catheter tube has at least one outlet port for a medical liquid at its distal end. It can however also have a plurality of outlet ports or a porous material through which the medical liquid can be released.

The outer catheter tube comprises two parts of differing rigidities, namely a flexible part and a rigid part. The rigidity of the flexible part is lower than the rigidity of the rigid part. The flexible part is located at the distal end of the outer catheter tube, i.e. closer to the tip of the catheter than the rigid part. In other words, the flexible part and the rigid part are located at different axial (or longitudinal) positions within along the outer catheter tube. The distal end of the flexible part is connected to the inner catheter tube. This means that no relative axial movement between the distal end of the flexible part and the inner catheter tube can occur. The medical catheter is designed such that the rigid part can perform an axial movement relative to the inner catheter tube. In other words, the rigid part is slidably attached to the inner catheter tube.

The medical catheter also comprises a drive means for generating a relative movement, in particular a relative axial movement, between the inner catheter tube and the rigid part of the outer catheter tube. This relative movement deforms the flexible part of the outer catheter tube such that it bulges outwards, thus increasing the outer diameter of the medical catheter. The bulged flexible part forms a seal between the medical catheter and the surrounding tissue, thus preventing backflow in the channel between the catheter and the tissue.

Numerous embodiments of the drive means are possible. In one embodiment, the drive means is a screw nut. This screw nut preferably engages a male thread on the outside of the inner catheter tube or an adaptor which is attached to the proximal end of the inner catheter tube. By turning the screw nut such that it moves towards the distal end of the medical catheter, the rigid part of the outer catheter tube is pushed towards the distal end of the inner catheter tube. If the screw nut is turned such that it moves towards the proximal end of the medical catheter, the rigid part of the outer catheter tube moves away from the distal end of the inner catheter tube, for example by a resilient force or by being pulled by the screw nut.

In a second embodiment, the drive means is a lever mechanism. The relative movement between the inner catheter tube and the rigid part of the outer catheter tube is generated by rotating the lever about its pivot point. In another embodiment, the drive means is a pinion drive and the inner catheter tube for example comprises a toothed rack which is engaged by a rack wheel which is attached to the rigid part of the outer catheter tube. The relative movement is generated by rotating the rack wheel. It is also possible to provide the toothed rack on the rigid part and the rack wheel on the inner catheter tube.

In general, a medical catheter is to be connected to a medical liquid delivering device such as a pump, a reservoir, a syringe or a conduit. The proximal end of the inner catheter tube is therefore preferably configured to be connected to the medical liquid delivering device. This connection is often implemented using a screw joint or a bayonet joint, such as a Luer taper (or Luer lock). In one embodiment, the drive means is a coupling mechanism which is configured to translate a relative movement between the inner catheter tube and the medical liquid delivering device, or a part of the medical liquid delivering device, during the connection process into the relative movement between the inner catheter tube and the rigid part of the outer catheter tube. If, for example, the screw of the screw joint or a bushing of the bayonet joint is moved so as to establish the connection between the medical catheter and the medical liquid delivering device, this automatically generates the relative movement by the rigid part of the outer catheter tube towards the distal end of the inner catheter tube. In this embodiment, a single manipulation of the medical catheter establishes the barrier to backflow and connects the catheter to the medical liquid delivering device. This reduces the trauma to the tissue into which the catheter is inserted.

The present invention also therefore relates to a system comprising a medical catheter and a medical liquid delivering device.

In one embodiment, the medical catheter comprises a biasing element which is configured to bias the rigid part of the outer catheter tube towards the proximal end of the inner catheter tube. The drive means thus has to apply a force larger than the force exerted by the biasing element in order to generate the relative movement between the inner catheter tube and the rigid part of the outer catheter tube. The biasing element straightens out the bulge in the flexible part of the outer catheter tube, such that the catheter can be inserted into or removed from the tissue without causing unnecessary damage.

In one embodiment, the flexible part of the outer catheter tube is ring-shaped. In other words, the flexible part has the shape of a hollow cylinder if no force is exerted on it by the rigid part. The flexible part optionally comprises a circular cut around its outer circumference, i.e. the cut extends from the outer surface of the flexible part into the flexible part. If the rigid part of the outer catheter tube is moved towards the distal end of the inner catheter tube, this causes the flexible part to be deformed, i.e. the flexible part bulges outwards as explained above. If the optional cut is provided, this deformation causes the cut to open, thus forming a gap which is open towards the distal end of the medical catheter. The flexible part on the outer side of the cut thus forms a lip which (radially) extends away from the inner catheter part. If, when delivered, the medical liquid flows back along the catheter, it fills the gap created by the cut and pushes the lip further outwards, thus further sealing the gap between the medical catheter and the surrounding tissue.

In a preferred embodiment, the circular cut is inclined relative to the surface normal of the outer surface of the flexible part, i.e. the cut is not a radial cut but rather encloses a certain angle, which is not equal to zero degrees, with the radial plane. Preferably, the cut inclines towards the proximal end of the flexible part as the distance from the outer surface increases.

This ensures that once the flexible part has been deformed, the opening of the slot is directed towards the distal end of the catheter.

Preferably, the outer end of the cut, i.e. the end of the cut at the outer surface of the flexible part, is closed by a predetermined breaking point. This ensures that the cut does not open to form a slot or gap while the medical catheter is being inserted into the tissue, which could then act as a barbed hook. The predetermined breaking point is preferably designed to break once the flexible part has reached a certain degree of deformation.

In another embodiment, the flexible part is configured to snap over if the relative movement between the rigid part of the outer catheter tube and the inner catheter tube exceeds a predetermined threshold. In particular, the flexible part snaps over towards the distal end of the medical catheter. By snapping over, the flexible part forms a circular lip which surrounds a circular slot between the lip and the inner catheter tube. If, when delivered, the medical liquid then flows back into the slot, it exerts a force on the lip, thus forcing the lip outwards towards the tissue and thereby further sealing the gap between the medical catheter and the tissue.

The distal flange of the flexible part is preferably rounded in order to reduce the trauma to the tissue when the medical catheter is inserted.

Numerous ways of connecting the distal end of the flexible part to the inner catheter tube are possible. In one embodiment, the distal end of the flexible part is glued or welded to the inner catheter tube. In another embodiment, the distal end of the flexible part engages a groove in the inner catheter tube. When the rigid part of the outer catheter tube is moved towards the distal end of the inner catheter tube, the distal flange of the flexible part is pushed into the groove, thus preventing the distal flange from moving axially relative to the inner catheter tube. In yet another embodiment, the distal end of the flexible part engages a shoulder on the outer circumference of the inner catheter tube. In yet another embodiment, the distal end of the flexible part is press-fitted onto the inner catheter tube. It is of course also possible to combine two or more of these embodiments.

The present invention also relates to a method for preventing backflow by a medical liquid along a catheter as described above, said method comprising the step of using the drive means to generate a relative movement of the rigid part of the outer catheter tube towards the distal end of the inner catheter tube in order to deform the flexible part such that it bulges outwards and thus forms a seal which prevents a backflow of the medical liquid.

Different embodiments or features of the embodiments described in this document can be combined in accordance with the invention wherever this is technically sensible and feasible. In particular, a feature of one embodiment can be replaced with another feature of another embodiment which has the same or a similar function. A feature of one embodiment which would imbue another embodiment with an additional function can also accordingly be added to said other embodiment.

Figure 2:
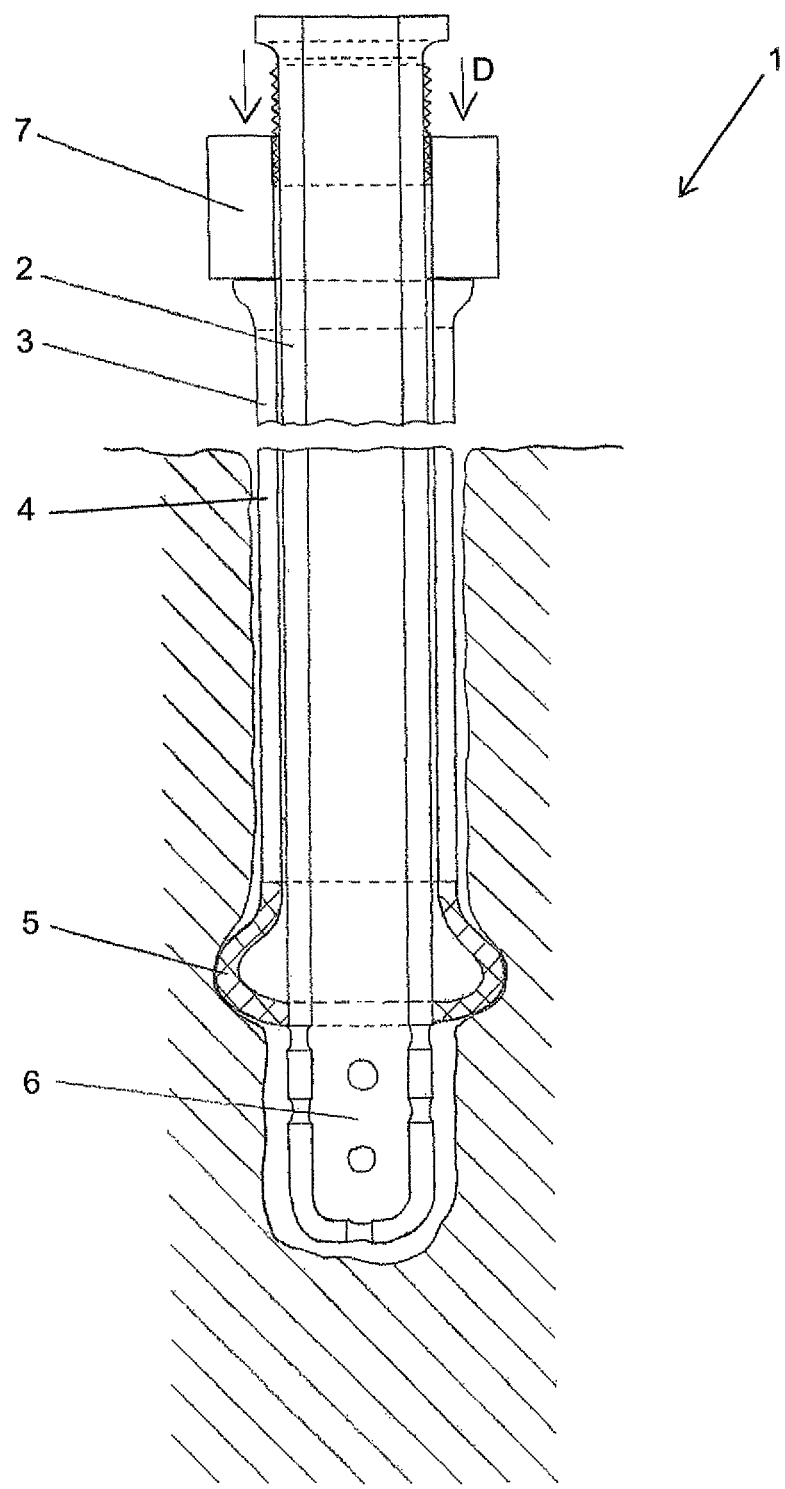
Figure 3:
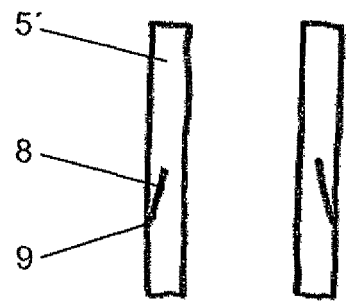
Figure 4:
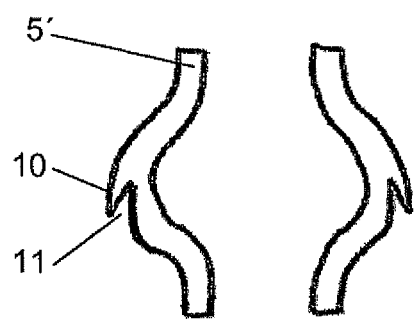

The present invention shall now be explained in more detail with reference to the appended figures, which show:

FIG. 1 a cross-sectional view of an example catheter, in a first state;

FIG. 2 the catheter of FIG. 1, in a second state;

FIG. 3 an alternative flexible part, in the first state;

FIG. 4 the flexible part of FIG. 3, in a second state; and

Figure 5:
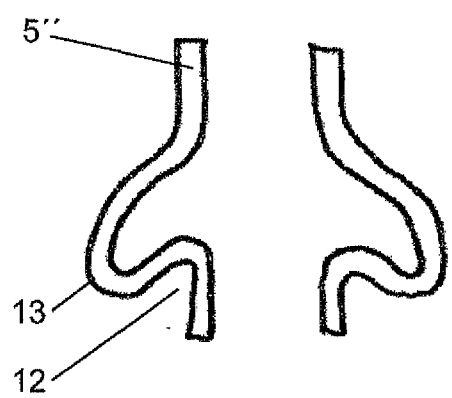

FIG. 5 another alternative flexible part.

FIG. 1 shows a cross-sectional view of a medical catheter 1. The catheter 1 comprises an inner catheter tube 2 and an outer catheter tube 3. The distal end of the inner catheter tube 2 has a plurality of outlet ports 6 for a medical liquid which is supplied at the proximal end of the inner catheter tube 2. The outer catheter tube 3 coaxially surrounds most of the inner catheter tube 2, save the distal end comprising the ports 6.

The outer catheter tube 3 consists of a rigid part 4 and a flexible part 5, wherein the rigidity of the flexible part 5 is lower than the rigidity of the rigid part 4. The rigidity of the flexible part 5 is also lower than the rigidity of the inner catheter tube 2. The distal end of the flexible part 5 is glued or welded to the inner catheter tube 2; for example, at most 25%, 10%, 5%, 2% or 1% of the axial extension of the flexible part 5 is glued or welded to the inner catheter tube 2. The distal end of the flexible part 5 is rounded in order to reduce trauma when the medical catheter 1 is introduced into the tissue T.

The rigid part 4 and the flexible part 5 are adjoining and may or may not be connected, for example glued or welded, together.

The position of the distal end of the flexible part 5 is more proximal than the most proximal port 6, such that no port 6 is covered by the outer catheter tube 3.

A screw nut 7 is provided at the proximal end of the outer catheter tube 3 and interacts with a male thread on the outer surface of the inner catheter tube 2.

In its first state as shown in FIG. 1, the medical catheter 1 is introduced into the tissue T. As it is introduced, a gap or channel is formed between the tissue T and the catheter 1. Any medical liquid administered through the ports 6 will therefore not only diffuse into the tissue T but also flow back along the catheter 1 through said channel.

The outer catheter tube 3 surrounds the inner catheter tube 2 in such a way that a relative axial movement, i.e. in the proximal-distal direction, between the rigid part 4 and the inner catheter tube 2 is possible.

FIG. 2 shows the catheter 1 of FIG. 1 in a second state. As compared to the state shown in FIG. 1, the screw nut 7 has been turned such that it has moved in the axial direction relative to the inner catheter tube 2, in the direction of the arrows D. During this movement, the screw nut 7 has pushed the rigid part 4 of the outer catheter tube 3 towards the distal end of the inner catheter tube 2. Since the distal end of the flexible part 5 is glued or welded to the inner catheter tube 2, the flexible part 5 has not been moved along with the rigid part 4 but has instead been deformed. This deformation has changed the shape of the flexible part 5 from a hollow cylinder to a bulge. The deformed flexible part 5 pushes against the tissue T and thus seals off the backflow channel from the outlet ports 6. The backflow of medical liquid is thus effectively prevented.

In order to remove the medical catheter 1 from the tissue T, the screw nut 7 is rotated such that it moves axially towards the proximal end of the inner catheter tube 2. This causes a relative axial movement of the rigid part 4 along the inner catheter tube 2 towards the proximal end of the catheter 1, either by the rigid part 4 being coupled to the screw nut 7 or by the rigid part 4 being pushed by the resilient force of the deformed flexible part 5 or by the force of a biasing element (not shown) or by any combination of the above.

FIG. 3 shows an alternative flexible part 5' in a first state. The flexible part 5' comprises a circular cut 8 which begins at the outer surface of the flexible part 5' and extends into the flexible part 5'. The end of the cut 8 at the outer surface of the flexible part 5' is referred to as the outer end 9. The cut 8 is not a radial cut but is rather inclined with respect to the radius of the flexible part 5'. Preferably, the cut 8 extends towards the proximal end of the flexible part 5' as it extends into the flexible part 5', starting at the outer end 9.

FIG. 4 shows the flexible part 5' in a second, deformed state, which is caused by a relative axial movement between the rigid part 4 and the inner catheter tube 2 in a similar way to the process described above. When the flexible part 5' is deformed, the cut 8 in the material of the flexible part 5' becomes wider and forms a groove 11 and a lip 10. Both the lip 10 and the groove 11 are circular in the cross-sectional plane of the catheter 1. When medical liquid is delivered through the outlet ports 6, the liquid is pushed into the groove 11, thereby pressing the lip 10 further into the tissue T. The higher the pressure of the medical liquid, the greater the force with which the lip 10 is pushed into the tissue T and the greater the effectiveness of the seal.

The outer end 9 of the cut 8 is closed by a predetermined breaking point which prevents the cut 8 from opening and thus forming the lip 10 and the groove 11 while the catheter 1 is still being introduced into the tissue T. The predetermined breaking point is broken when the flexible part 5' is deformed by the relative axial movement between the rigid part 4 and the inner catheter tube 2.

FIG. 5 shows another alternative flexible part 5", in its deformed shape. In its initial shape, the flexible part 5" also resembles a hollow cylinder. As the flexible part 5" is deformed, a part of it snaps over and forms a circular groove 12 and a fold 13. Instead of snapping over, the flexible part 5" can also be designed such that the groove 12 is formed continuously as the flexible part 5" is deformed. In a similar way to the flexible part 5', medical liquid which is delivered through the outlet ports 6 flows into the groove 12 and pushes the fold 13 into the tissue T. As the pressure of the medical liquid increases, so the force with which the fold 13 is pushed into the tissue T also increases, thus improving the sealing properties of the flexible part 5".

An adaptor can be used to assemble multiple parts of the catheter or to attach the catheter to another device. Such an adaptor is also part of the present invention. An adaptor for fixing a (medical) apparatus to one or two support structures is characterised in that the adaptor is constructed in three parts from a bearing part and two support parts, wherein the bearing part can be connected to the medical apparatus, the first support part can be connected to a first support structure, and the second support part can be connected to a second support structure, and wherein the adaptor can assume at least three states: a first state, in which the bearing part is connected, free of clearance, to the first support part only; a second state, in which the bearing part is connected, free of clearance, to the second support part only; and a third state, in which the bearing part is connected, free of clearance, to the first support part and the second support part.

The invention claimed is:

1. A medical catheter comprising an inner catheter tube defining a longitudinal axis and an outer catheter tube, wherein the inner catheter tube has at least one outlet port for a medical liquid at its distal end and the outer catheter tube comprises two parts of differing rigidities, namely a flexible part and a rigid part, wherein the flexible part is located at the distal end of the outer catheter tube and the distal end of the flexible part is connected to the inner catheter tube, wherein the medical catheter also comprises a drive means for generating a relative movement between the inner catheter tube and the rigid part of the outer catheter tube and wherein the flexible part is cylindrical and comprises a circular cut around its outer circumference, wherein the circular cut is inclined relative to a surface normal of an outer surface of the flexible part, and wherein selective relative motion between the outer catheter tube and the inner catheter tube deforms the flexible part such that it bulges radially outwardly relative to the longitudinal axis causing the circular cut to open forming a circular lip and a circular groove having an opening directed towards the at least one outlet port, whereby the medical liquid being communicated from the at least one outlet port is pushed into the circular groove urging the circular lip further outwardly.

2. The medical catheter of claim 1, wherein the drive means is a screw nut.

3. The medical catheter of claim 1, wherein an outer end of the cut is closed by a predetermined breaking point.

4. The medical catheter of claim 1, wherein the flexible part is configured to snap over if the relative movement between the rigid part of the outer catheter tube and the inner catheter tube exceeds a predetermined threshold.

5. The medical catheter of claim 1, wherein the distal end of the flexible part is glued to the inner catheter tube.

6. The medical catheter of claim 1, wherein the distal end of the flexible part engages a groove in the inner catheter tube.

7. The medical catheter of claim 1, wherein the distal end of the flexible part engages a shoulder on the outer circumference of the inner catheter tube.

8. The medical catheter of claim 1, wherein the distal end of the flexible part is press-fitted onto the inner catheter tube.

9. A method for preventing backflow by a medical liquid along a catheter as claimed in claim 1, said method comprising the step of using the drive means to generate a relative movement of the rigid part of the outer catheter tube towards the distal end of the inner catheter tube in order to deform the flexible part such that it bulges outwards and thus forms a seal which prevents a backflow of the medical liquid.

10. A medical catheter comprising:
an inner catheter tube having opposite proximal and distal ends, the inner catheter tube defining a longitudinal axis and at least one outlet port at the distal end thereof for selective communication of an associated medical liquid through the at least one outlet port; and
an outer catheter tube carried on the inner catheter tube, the outer catheter tube comprising:
a rigid portion operatively slidably coupled with the inner catheter tube enabling selective relative motion between the inner and outer catheter tubes in directions substantially parallel to the longitudinal axis of the inner catheter tube; and
a flexible portion having opposite proximal and distal ends, the proximal end of the flexible portion being coupled with the rigid portion of the outer catheter tube, and the distal end of the flexible portion being coupled with a portion of the inner catheter tube between the proximal end of the inner catheter tube and the at least one outlet port, the flexible portion defining a circular cut on an outer surface thereof and being directed at a non-zero angle relative to a surface normal of the outer surface, wherein selective relative motion between the outer catheter tube and the inner catheter tube deforms the flexible portion such that it bulges radially outwardly relative to the longitudinal axis causing the circular cut to open forming a circular lip and a circular groove having an opening directed towards the at least one outlet port whereby ale associated medical fluid being communicated from the at least one outlet port is pushed into the circular groove urging the circular lip further outwardly.

11. The medical catheter according to claim 10, further comp rising:
   a drive means for generating the relative movement between the inner and outer catheter tubes.

12. The medical catheter according to claim 11, wherein the drive means comprises a screw nut.

13. The medical catheter according to claim 10, wherein the distal end of the flexible portion engages a groove defined in the inner catheter tube.

* * * * *